United States Patent

Coy et al.

[11] 4,180,501
[45] Dec. 25, 1979

[54] BIS (POLYPEPTIDE) DERIVATIVES OF ENKEPHALIN

[76] Inventors: David H. Coy, 4319 Perrier St., New Orleans, La. 65115; Abba J. Kastin, 4400 Morales St., Metairie, La. 70002

[21] Appl. No.: 915,981

[22] Filed: Jun. 16, 1978

[51] Int. Cl.$^2$ .................... C07C 103/52; A61K 37/00
[52] U.S. Cl. .............................. 260/112.5 R; 424/177
[58] Field of Search ................. 260/112.5 R; 424/177

[56] References Cited
PUBLICATIONS
C. R. Beddell, et al., Proc. B. Soc. Lond. B. 198, 249–265 (1977).

Primary Examiner—Delbert R. Phillips
Attorney, Agent, or Firm—Kinney & Niblack

[57] ABSTRACT

Bis-(polypeptide) derivatives represented by the formulae:

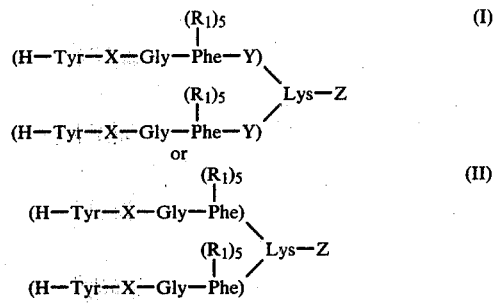

wherein: X is glycine or a chiral residue of a D-amino acid selected from the group consisting of D-alanine, D-leucine, D-isoleucine, D-valine, D-norvaline, D-phenylalanine, D-tyrosine, D-tryptophan, D-serine, D-threonine, D-methionine, D-glutamic acid, D-glutamine, D-aspartic acid, D-asparagine, D-lysine, D-proline, D-histidine and D-arginine; Y a residue of methionine or leucine and Z is selected from the group consisting of hydroxy, amino, loweralkylamino, diloweralkylamino and loweralkoxy; each $R_1$ is hydrogen or fluorine and the pharmaceutically acceptable salts thereof; intermediates useful in making the novel pentapeptides and pharmaceutical compositions and methods employing them.

15 Claims, No Drawings

BIS (POLYPEPTIDE) DERIVATIVES OF ENKEPHALIN

BACKGROUND OF THE INVENTION

While there are a number of analgesic agents currently utilized to relieve mild to severe pain, the search for improved analgesics is a continuing one because of the numerous problems associated with the presently available agents. Aspirin and related salicylates are considered to be non-narcotic analgesic agents useful for relieving mild to moderate pain in addition to their usefulness as anti-inflammatory and anti-pyretic agents. However, the ingestion of salicylic acid or related salicylates may result in epigastric distress, nausea and vomiting. This widely used class of non-narcotic analgesic agents may also cause gastric ulceration and even hemorrage both in experimental animals and man. Exacerbation of peptic ulcer symptoms and erosive gastritis have all been reported in patients on high dose therapy, i.e., arthritis patients. Aspirin is also one of the most common causes of drug poisoning in young children and has a potential of serious toxicity if used improperly.

Acetaminophen is also considered to be a non-narcotic analgesic agent useful in treating mild pain associated with simple headache, common muscular aches, etc. While acetaminophen is particularly useful for patients who cannot take aspirin, i.e., ulcer patients, its use is contraindicated in individuals who have exhibited a sensitivity to it. In addition to their drawbacks in view of their potential side effects, the mild non-narcotic analgesic agents are not sufficiently potent to relieve the severe pain associated with surgery, cancer and the like.

Unfortunately, the potent analgesic agents capable of relieving such severe pain are also narcotic agents and their use entails the risk of producing physical and sometimes psychological dependence. There are as yet no agents effective against severe pain that are entirely free of this risk.

Thus, there is an urgent need for improved analgesic agents for treating mild as well as severe pain. The present invention provides such agents.

In addition to the need for improved analgesic agents, there is also a need for improved psychotropic agents to replace or to provide an alternative to current therapy. The compounds of this invention, in addition to their analgesic activity, also exhibit anti-depressant activity. Thus their usefulness as analgesic agents is enhanced since many patients suffering from pain also exhibit varying states of anxiety and depression.

In 1975, Hughes et al. identified a pentapeptide, methionine enkephalin, which has the following structure, H-Tyr-Gly-Gly-Phe-Met-OH [see Hughes et al., Nature, 258, 577 (1975)]. This peptide is found in many areas of the brain where it appears to act as a neurotransmitter or neuromodulator in a central pain suppressive system. The natural peptide binds stereospecifically to partially purified brain opiate receptor sites [for instance see Bradbury et al., Nature, 260, 793 (1976)], is very active in bioassays for opiate activity, but exhibits only weak analgesic activity of short duration when injected directly into the brain of the rat, [for instance, see Belluzzi et al., Nature, 260, 625 (1976)].

We subsequently found that when methionine enkephalin was substituted in the 2-position with a D-amino acid, potent analgesic agents are obtained. The D-amino acid[2] analogs also exhibit other central nervous system and hormonal activities.

We have now found that even greater in vivo analgesia is obtained when two D-amino acid[2]-enkephalins or a tetra peptide having the first four amino acid residues as D-amino acid[2]-enkephalin are joined to the N-terminis of lysine or a lysine derivative.

SUMMARY OF THE INVENTION

This invention relates to novel polypeptides, and more specifically relates to improved $N^\alpha$, $N^\epsilon$ bis substituted lysine and lysine derivatives which are useful as analgesic and anti-depressant agents, tranquilizers, sedative-hypnotics, growth hormone promoters and prolactin releasing agents, to intermediates useful in the preparation of the novel polypeptides, and to pharmaceutical compositions and methods employing such novel pentapeptides.

Specifically, the novel polypeptides are bis (enkephalin) derivatives.

DETAILED DESCRIPTION OF PREFERRED EMBODIMENTS

The compounds of this invention are represented by formulae I and II:

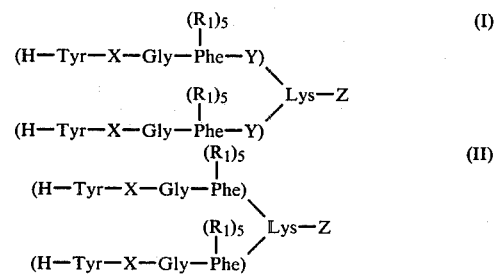

wherein X is glycine or a chiral residue of a D-amino acid selected from the group consisting of D-alanine, D-leucine, D-isoleucine, D-valine, D-norvaline, D-phenylalanine, D-tyrosine, D-tryptophan, D-serine, D-threonine, D-methionine, D-glutamic acid, D-glutamine, D-aspartic acid, D-asparagine, D-lysine, D-proline, D-histidine and D-arginine; and Y is a residue of methionine or leucine and Z is selected from the group consisting of hydroxy, amino, loweralkylamino, diloweralkylamino and lower alkoxy; and the pharmaceutically acceptable salts thereof.

The term "pharmaceutically acceptable salts," as used herein, refers to the non-toxic alkali metal, alkaline earth metal and ammonium salts commonly used in the pharmaceutical industry including the sodium, potassium, lithium, calcium, magnesium, barium and ammonium salts which are prepared by methods well known in the art. The term also includes non-toxic acid addition salts which are generally prepared by reacting the compounds of this invention with a suitable organic or inorganic acid. Representative salts include the hydrochloride, hydrobromide, sulfate, bisulfate, acetate, oxalate, valerate, oleate, laurate, borate, benzoate, lactate, phosphate, tosylate, citrate, maleate, fumarate, succinate, tartrate, napsylate and the like.

The term "lower alkyl" refers to straight and branched chain alkyl groups having from 1 to 6 carbon atoms such as methyl, ethyl, n-propyl, iso-propyl, n-butyl, sec-butyl, tert-butyl, n-pentyl, n-butyl and the like.

All chiral amino acid residues identified herein are in the natural or L-configuration unless otherwise specified.

In keeping with standard peptide nomenclature, abbreviations for chiral amino acid residues have been used herein as follows:

| | |
|---|---|
| His—L-histidine | D-His—D-histidine |
| Tyr—L-tyrosine | Ile—L-isoleucine |
| D-Tyr—D-tyrosine | D-Ile—D-isoleucine |
| Gly—glycine | Leu—L-leucine |
| Phe—L-phenylalanine | D-Leu—D-leucine |
| D-Phe—D-phenylalanine | Thr—L-threonine |
| Met—L-methionine | D-Thr—D-threonine |
| D-Met—D-metionine | Val—L-valine |
| Ala—L-alanine | D-Val—D-valine |
| D-Ala—D-alanine | Pro—L-proline |
| Ser—L-serine | D-Pro—D-proline |
| D-Ser—D-serine | Gln—L-glutamine |
| Lys—L-lysine | D-Gln—D-glutamine |
| D-Lys—D-lysine | Glu—L-glutamic acid |
| Asn—L-asparagine | D-Glu—D-glutamic acid |
| D-Asn—D-asparagine | Trp—L-tryptophan |
| D-Asp—D-aspartic acid | D-Trp—D-tryptophan, etc. |

Also contemplated within the scope of the present invention are intermediates of formula II:

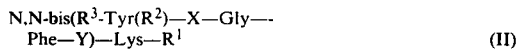

N,N-bis($R^3$-Tyr($R^2$)—X—Gly—Phe—Y)—Lys—$R^1$     (II)

wherein $R^1$ is selected from a group consisting of $NH_2$, OH, or a derivatized insoluble polystyrene resin support represented by the formulae III or IV as follows:

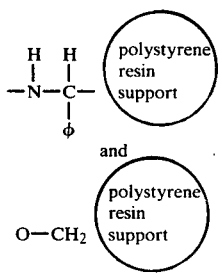

R² is a protecting group for the phenolic hydroxyl group of tyrosine selected from the group consisting of tetrahydropyranyl, tert-butyl, trityl, benzoyl, 2,4-dichlorobenzyl, benzyloxycarbonyl, and 2-bromobenzyloxycarbonyl (2-Br-Z);

R³ is a protecting group which would be used by one skilled in the art of solid-phase synthesis of the peptides (I) selected from the group consisting of acyl type protecting groups, aromatic urethan-type protecting groups, cycloalkyl urethan protecting groups, thio urethan type protecting groups, alkyl type protecting groups, trialkylsilane groups or aliphatic urethan protecting groups; and X is a D-amino acid as defined in formula (I) or, when X is D-tyrosine, D-threonine, D-serine, D-glutamic acid or D-lysine, a protected chiral amino acid residue as defined below.

When X is, D-tyrosine; the protected chiral residue is X(R²) wherein R² is as described hereinabove.

When X is D-serine or D-threonine, the protected residue is X(R₂) wherein R₂ is a protecting group for the alcoholic hydroxyl function and is as defined above.

When X is D-glutamic acid, D-aspartic acid, the protected residue is X(R₄) wherein R₄ is benzyl or tertbutyl. In the case of D-lysine, the protected redidue is X(R₅) wherein R₅ is a protecting group for the epsilon amino function selected from the group consisting of benzyloxycarbonyl or 2-chlorobenzyloxycarbonyl.

When X is as D-arginine, the protected residue is X(R₆) wherein R₆ is a protecting group for the guanidino function such as tosyl or nitro.

The term "acyl type protecting groups" refers to groups illustrated but not restricted to formyl, trifluoroacetyl, tosyl, nitrosulfonyl, and the like.

The term "aromatic urethan-type protecting groups" is represented by groups such as benzyloxycarbonyl, p-methoxybenzyloxycarbonyl, p-biphenyl isopropyloxycarbonyl, 2,5-dimethoxyphenyl isopropyloxycarbonyl, and the like.

The term "cycloalkyl urethan protecting group", as used herein, refers to groups such as cyclopentyloxycarbonyl, adamantyloxycarbonyl, cyclohexylcarbonyl, isobornyloxycarbonyl, etc.

"Urethan type protecting groups" include but are not limited to groups such as phenylthiocarbonyl.

"Alkyl type protecting groups" are those commonly used in the art such as trityl.

"Trialkysilane groups" include compounds such as trimethylsilane, triethylsilane, tributylsilane, and the like.

The preferred protecting groups, the "aliphatic urethan protecting groups" include tert-butyloxycarbonyl, diisopropyloxycarbonyl, isopropyloxycarbonyl, allyloxycarbonyl and the like.

The polystyrene resin support is preferably a copolymer of styrene with about 1–2% divinyl benzene as a cross-linking agent which causes the polystyrene polymer to be completely insoluble in most organic solvents. In formula III, φ is phenyl.

In selecting a particular side-chain protecting group to be used in the synthesis of the peptides of formula I, several conditions must be met: (a) the protecting group must be stable to the reagent and under reaction conditions selected for removing the α-amino protecting group at each step of the synthesis; (b) the protecting group must retain its protecting properties and not be chemically modified; and (c) the side-chain protecting group must be removable at the end of the solid-phase synthesis under reaction conditions that will not alter the peptide chain.

The pentapeptides of formulae (I) and (II) are prepared using standard solid-phase techniques. The synthesis is commenced from the C-terminal end of the peptide using an α-amino protected resin. A suitable starting material can be prepared, for instance, by attaching an α,ε-amino protected lysine to a chloromethylated resin, a hydroxymethyl resin, or a benzhydrylamine resin. One such chloromethylated resin is sold under the tradename Bio-beads SX-1 by Bio Rad Laboratories, Richmond, California and the preparation of the hydroxymethyl resin is described by Bodanszky et al., *Chem. Ind.* (London) 38, 1597 (1966). The benzhydrylamine resin has been described by Pietta and Marshall, *Chem. Commun.*, 650 (1970) and is commercially available from Beckman Instrument, Palo Alto, California.

In the preparation of the compounds of this invention, the bis-t-Boc-derivative of lysine is coupled to the chloromethylated resin with the aid of, for example, cesium bicarbonate catalyst, according to the method described by Gisin, *Helv. Chim. Acta*, 56, 1476 (1973).

After the initial coupling, the amino protecting groups are removed by a choice of reagents including trifluoroacetic acid or hydrochloric acid solutions in organic solvents at room temperature. After removal of the amino protecting groups, the remaining protected amino acids are coupled stepwise in the desired order to obtain the compounds of formula II. Each protected amino acid is generally reacted in a 3-fold excess using an appropriate carboxyl group activator such as dicyclohexylcarbodiimide in solution in, for example, methylene chloride-dimethylformamide mixtures.

After the desired amino acid sequence has been completed, the desired peptide is removed from the resin support by treatment with a reagent such as hydrogen fluoride which not only cleaves the peptide from the resin, but also cleaves all remaining side-chain protecting groups. When the chloromethylated resin is used, hydrogen fluoride treatment results in the formation of the free peptide acids of formula I (Y=OH). When the benzhydrylamine resin is used, hydrogen fluoride treatment results directly in the free peptide amides of formula I (Y=NH$_2$). Alternatively, when the chloromethylated resin is employed, the side-chain protected peptide can be cleaved by treatment of the peptide-resin with ammonia to give the desired side-chain protected amide or with an alkylamine or dialkylamine to give a side-chain protected alkylamide or dialkylamide. Side-chain protection is then removed in the usual fashion by treatment with hydrogen fluoride to give the amides of formula I.

In preparing the esters of this invention (Z=lower alkoxy), the resin used to prepare the acids of formula I (Y=OH) is employed and the peptide is removed from the resin by treatment with base and the appropriate alcohol, i.e., methanol. Side chain protection is then removed in the usual fashion by treatment with hydrogen chloride to obtain the desired ester.

The solid-phase procedure discussed above is well known in the art and has been essentially described by J. M. Stewart, "Solid Phase Peptide Synthesis:" (Freeman and Co., San Francisco, 1969).

The compounds of formula I are useful as analgesic and anti-depressant agents when administered to mammalian hosts at dosages of from 0.0001 to 5 mg/kg of body weight daily, preferably in divided dosages. The compounds are preferably administered by parenteral routes, i.e., the intravenous, intraperitoneal, intramuscular or subcutaneous routes of administration. The compounds may also be administered by a variety of other routes including oral or sublingual, vaginal, rectal or nasal routes of administration. Accordingly, one aspect of the present invention includes pharmaceutical compositions suitable for such routes of administration.

The analgesic activity of the compounds of formula I is established in the rat tail flick test as described by D'Amour and Smith, *J. Pharmac. Exp. Ther.*, 72, 74 (1941).

The anti-depressant tranquilizing and sedative hypnotic activities are established in the open field test described by Kullarni et al. *Pharmakopsychiatrie News Psychopharmakologie* 8(1): pp 45–50 (1975) and the self stimulation test described by Bailey et al., *Research Communications in Chemical Pathology and Pharmacology* 11(4): pp 543–552 (1975). The release or radioimmuno assayable growth hormone and prolactin release after intracereoventribular injection in rats was also assayed.

The following examples further illustrate the present invention.

EXAMPLE 1

Preparation of N$^\alpha$,N$^\epsilon$-bis (o-2-bromobenzyloxycarbonyl-L-tyrosyl-D-alanyl-glycyl-L-phenylalanyl-L-methionyl)-2-chlorobenzyloxycarbonyl-L-lysyl-benzhydrylamine resin.

Benzhydrylamine resin (1.88 g., 1.0 mmole), purchased from Beckman Instruments, Palo Alto, California, was placed in the reaction vessel of a Beckman Model 990 automatic peptide synthesizer, programmed to carry out the following cycle of washes and reactions: (a) methylene chloride; (b) 33% trifluoroacetic acid in methylene chloride (2 times for 2.5 and 25 minutes each); (c) methylene chloride; (d) ethanol; (e) chloroform; ((f) 10% triethylamine in chloroform (2 times for 5 minutes each)); (g) chloroform; and (h) methylene chloride.

The free amino resin was then stirred with N$^\alpha$,N$^\epsilon$-bis-tert-butyloxycarbonyl(t-Boc)lysine (1.04 g., 3.0 mmoles) in methylene chloride, and diclohexylcarbodiimide (3.0 mmoles) was added thereto. The mixture was stirred at room temperature for 2 hours and the peptide resin was then washed successively with methylene chloride (3 times), ethanol (3 times), and methylene chloride (3 times). The attached amino acid was deprotected with 33% trifluoroacetic acid in methylene chloride (2 times for 2.5 and 25 minutes each) and then steps (c) through (h) as described in the above wash were performed.

The following amino acids (6.0 mmoles) were then coupled successively by the same cycle of events: t-Boc-phenylalanine, glycine, t-Boc-D-alanine and t-Boc-tyrosine (2-Br-Z). The completed, dried peptide resin weighed 3.43 g.

EXAMPLE 2

Preparation of N$^\alpha$,N$^\epsilon$-bis(L-tyrosyl-D-alanyl-glycyl-L-phenylalanyl-L-methionyl)-L-lysine amide.

The branched-chain peptide amide was deprotected and cleaved from the resin support of Example 1 by treating the resin with hydrogen fluoride (20 ml) and anisole (2 ml) at 0° C. for 45 minutes. The hydrogen fluoride was removed at reduced pressure and the anisole removed by washing with ethyl acetate.

The crude peptide was purified by gel filtration on a column of Sephadex G-25 (2.5×95 cm) by elution with 0.2 molar acetic acid followed by partition chromatography on Sephadex G=25 using 1-butanol:acetic acid:-water (4:1:5) as the eluant. The peptide was obtained as a fluffy white powder (290 mg.).

The product was homogeneous by thin layer chromatography using the spray reagents and solveny systems described in Example 2: (A), 0.32; (B), 0.88; (C), 0.59; (D), 0.64. Amino acid analysis gave: Gly, 1.96; Ala, 2.00; Met, 1.52; Tyr, 2.00; Phe, 2.06; Lys, 1.00.

EXAMPLE 3

Preparation of N$^\alpha$,N$^\epsilon$-bis(o-2-bromobenzyloxycarbonyl-L-tyrosyl-D-alanyl-glycyl-L-phenylalanyl)-2-chlorobenzyloxycarbonyl-L-lysyl-benzhydrylamine resin.

Using the conditions described in Examples 1 and 2, the Boc derivatives (6.0 mmoles) of phenylalanine, glycine, D-alanine and tyrosine (2-Br-Z) were coupled successively to Lys-benzhydrylamine resin (1.0 mmole). The completed, dried peptide resin weighed 3.28 g.

EXAMPLE 4

Preparation of
$N^\alpha,N^\epsilon$-bis(L-tyrosyl-D-alanyl-glycyl-L-phenylalanyl)-L-lysine amide.

The branched chain peptide amide was deprotected and cleaved from the resin support of Example 3 under the conditions described in Example 2. The crude material was purified by gel filtration and partition chromatography as described in Example 2 to yield a white, fluffy powder (440 mg).

The product is homogeneous by thin layer chromatography using the spray reagents and solveny systems described in Example 2: (A), 0.27; (B) 0.84; (C), 0.56; (D), 0.63. Amino acid analysis gave: Gly, 1.97; Ala, 2.04; Tyr, 2.00; Phe, 2.04; Lys, 1.01.

The present invention includes within its scope pharmaceutical compositions comprising, as an active ingredient, at least one of the compounds of formula I in association with a pharmaceutical carrier or diluent. The compounds of this invention can be administered by oral, parenteral, nasal, vaginal, rectal or sublingual routes of administration and can be formulated in dosage forms appropriate for each route of administration.

Solid dosage forms for oral administration include capsules, tablets, pills, powders and granules. In such solid dosage forms, the active compound is admixed with at least one inert diluent such as sucrose, lactose, or starch. Such dosage forms can also comprise, as is normal practice, additional substances other than inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include pharmaceutically acceptable emulsions, solutions, suspensions, syrups, and elixirs containing inert diluents commonly used in the art, such as water. Besides, inert diluents, such compositions can also include adjuvants, such as wetting agents, emulsifying and suspending agents, and sweetening, flavoring, and perfuming agents.

Preparations according to this invention for parenteral administration include sterile aqueous or nonaqueous solutions, suspensions, or emulsions. Examples of non-aqueous solvents or vehicles are propylene glycol, polyethylene glycol, vegetable oils, such as olive oil, and injectable organic esters such as ethyl oleate. Such dosage forms may also contain adjuvants such as preserving, wetting, emulsifying, and dispersing agents. They may be sterilized by, for example, filtration through a bacteria-retaining filter, by incorporating sterilizing agents into the compositions, by irradiating the compositions, or by heating the compositions. They can also be manufactured in the form of sterile solid compositions which can be dissolved in sterile water, or some other sterile injectable medium immediately before use.

Compositions for rectal or vaginal administration are preferably suppositories which may contain, in addition to the active substance, excipients such as cocoa butter or a suppository wax.

Compositions for nasal or sublingual administration are also prepared with standard excipients well known in the art.

The dosage of active ingredient in the compositions of this invention may be varied; however, it is necessary that the amount of the active ingredient shall be such that a suitable dosage form is obtained. The selected dosage depends upon the desired therapeutic effect, on the route of administration, and on the duration of the treatment. Generally, dosage levels of between 0.0001 to 5.0 mg./kg. of body weight daily are administered to mammals to obtain effective relief from pain or to relieve depression.

The following examples further illustrate the pharmaceutical compositions which are a feature of this invention.

EXAMPLE 9

Tablets weighing 200 mg. and having the following compositions are formulated:

| Ingredient | Mg |
| --- | --- |
| $N^\alpha,N^\epsilon$-bis(L-tyrosyl-D-alanyl-L-glycyl-L-phenylalanyl-L-methionine enkephalin)-L-lysine amide | 25 |
| Starch | 145 |
| Colloidal silica | 27 |
| Magnesium stearate | 3 |

EXAMPLE 10

Sterile 10 ml. ampoules can be prepared containing 1 mg per ml of $N^\alpha,N^\epsilon$-bis(L-tyrosyl-D-alanyl-L-glycyl-L-phenylalanyl-L-methionine enkephalin)lysine amide, 0.1 percent sodium bisulfate, 0.7 percent sodium chloride, and 0.5 percent chlorobutanol as a preservative.

EXAMPLE 11

Topical aqueous formulations for administration by nose drops or nasal spray are formulated containing 1 mg of $N^\alpha,N^\epsilon$-bis(L-tyrosyl-D-leucyl-L-glycyl-L-phenylalanyl-L-leucine enkephalin)lysine amide, 3.8 mg. glycerine, 40 mg. sorbital, 0.02 mg. benzalkonium chloride and purified water q.s. 1 ml.

We claim:

1. A polypeptide of the formulae

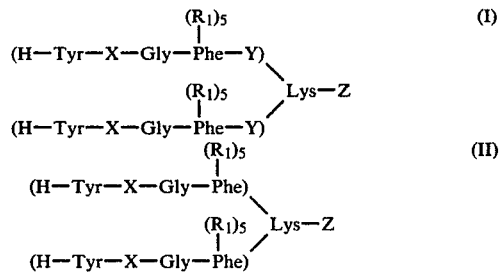

wherein: X is a chiral residue of a D-amino acid selected from the group consisting of D-alanine, D-leucine, D-isoleucine, D-valine, D-norvaline, D-phenylalanine, D-tyrosine, D-tryptophan, D-serine, D-threonine, D-methionine, D-glutamic acid, D-glutamine, D-aspartic acid, D-asparagine, D-lysine, D-proline, D-histidine and D-arginine; Y is methionine or leucine and Z is selected from the group consisting of hydroxy, amino, loweralkylamino, diloweralkylamino and loweralkoxy; and the pharmaceutically acceptable salts thereof; $R_1$ is hydrogen or fluorine.

2. A compound of claim 1 wherein Y is methionine.

3. A compound of claim 2 wherein Z is hydroxy.

4. A compound of claim 2 wherein Z is amino.

5. A compound of claim 2 wherein Z is loweralkylamino.

6. A compound of claim 2 wherein Z is diloweralkylamino.

7. A compound of claim 1 wherein Z is loweralkoxy.

8. A compound of claim 4: $N^\alpha,N^\epsilon$-bis(Tyr-D-Ala-Gly-Phe-Met)lysine amide or a pharmaceutically acceptable salt thereof.

9. A compound of claim 1 wherein Y is leucine.

10. A compound of claim 9 wherein X is hydroxy.

11. A compound of claim 10 wherein X is amino.

12. A compound of claim 10 wherein X is loweralkylamino.

13. A compound of claim 10 wherein X is diloweralkylamino.

14. A compound of claim 10 wherein X is loweralkoxy.

15. A pharmaceutical composition comprising administering an effective amount of a compound of claim 1 and a pharmaceutically acceptable carrier or diluent.

* * * * *